(12) United States Patent
Kim et al.

(10) Patent No.: US 11,590,256 B2
(45) Date of Patent: Feb. 28, 2023

(54) MEDICAL MATERIAL PRODUCED USING COLLAGEN AND METHOD FOR PRODUCING SAME

(71) Applicant: SEWONCELLONTECH CO., LTD., Seoul (KR)

(72) Inventors: Jin Sub Kim, Seoul (KR); Ji Chul Yoo, Namyangju-si (KR); Dong Sam Suh, Seoul (KR); Cheong Ho Chang, Seoul (KR)

(73) Assignee: CELLONTECH CO., LTD., Seoul (KR)

( * ) Notice: Subject to any disclaimer, the term of this patent is extended or adjusted under 35 U.S.C. 154(b) by 291 days.

(21) Appl. No.: 16/759,220

(22) PCT Filed: Nov. 10, 2017

(86) PCT No.: PCT/KR2017/012718
§ 371 (c)(1),
(2) Date: Apr. 24, 2020

(87) PCT Pub. No.: WO2019/088331
PCT Pub. Date: May 9, 2019

(65) Prior Publication Data
US 2020/0316247 A1    Oct. 8, 2020

(30) Foreign Application Priority Data
Nov. 3, 2017 (KR) .................. 10-2017-0146201

(51) Int. Cl.
*A61L 17/08*    (2006.01)
*A61L 27/24*    (2006.01)
*D01D 5/00*    (2006.01)

(52) U.S. Cl.
CPC .............. *A61L 17/08* (2013.01); *A61L 27/24* (2013.01); *D01D 5/0015* (2013.01); *D10B 2211/06* (2013.01)

(58) Field of Classification Search
CPC .............. D01D 5/0007; D01D 5/0061; A61L 31/044; A61L 27/24
See application file for complete search history.

(56) References Cited

U.S. PATENT DOCUMENTS

| | | | | |
|---|---|---|---|---|
| 6,977,231 B1* | 12/2005 | Matsuda | ................. | B32B 9/047 606/228 |
| 2008/0268052 A1* | 10/2008 | Voytik-Harbin | ........ | A61L 27/24 424/548 |
| 2009/0136651 A1* | 5/2009 | Larsen | ................. | A61K 38/363 427/2.31 |
| 2017/0247430 A1* | 8/2017 | Yost | ....................... | C07K 14/78 |

FOREIGN PATENT DOCUMENTS

| | | |
|---|---|---|
| JP | 07-083759 B2 | 9/1995 |
| JP | 2000-271207 A | 10/2000 |
| JP | 2016-069783 A | 5/2016 |
| KR | 2001-0090876 A | 10/2001 |
| KR | 2013-0066581 A | 6/2013 |
| KR | 10-1473617 B1 | 12/2014 |
| KR | 2016-0032569 A | 3/2016 |
| KR | 10-2016-0081940 A | 7/2016 |

OTHER PUBLICATIONS

EntoKey:Hyperosmotic agents, 2 pages (https://entokey.com/hyperosmotic-agents-2/).*
Na, G. C. et al., "In Vitro Collagen Fibril Assembly in Glycerol Solution: Evidence for a Helical Cooperative Mechanism Involving Microfibrils", Biochemistry, 1986, vol. 25. pp. 958-966.
Alvin T. Yeh et al., "Reversible Dissociation of Collagen in Tissue", The Society for Investigative Dermatology, Dec. 2013, pp. 121:1332-1335, vol. 121, No. 6.

* cited by examiner

*Primary Examiner* — Kyle A Purdy
(74) *Attorney, Agent, or Firm* — Novick, Kim & Lee PLLC; Jae Youn Kim (57) ABSTRACT

Disclosed is a medical material manufactured using collagen and a method of manufacturing the same. The method includes (1) preparing collagen using distilled water as a solvent, (2) filling a syringe with the prepared collagen and then spinning the collagen through a syringe needle, (3) immediately immersing the spun collagen in a cross-linking solution, which is a mixture including therein a hyperosmotic agent and a cross-linking agent mixed with each other, (4) removing and then washing the collagen after cross-linking is completed, and (5) removing and then drying the collagen after the washing is completed. When the collagen is spun and processed into the form of a thread and the spun thread is then cross-linked, the cross-linked collagen thread has increased strength compared to before cross-linking, and the shape thereof is retained in an aqueous solution.

13 Claims, 11 Drawing Sheets

No structural fluidity after cross-linking

FIG. 11

MEDICAL MATERIAL PRODUCED USING COLLAGEN AND METHOD FOR PRODUCING SAME

TECHNICAL FIELD

An embodiment of the present invention relates to a medical material manufactured using collagen and a method of manufacturing the same. More particularly, when the collagen is spun and processed into the form of a thread and when the spun thread is then cross-linked, the cross-linked collagen thread has increased strength compared to before cross-linking, and the shape thereof is retained in an aqueous solution. Accordingly, various applications thereof as a medical thread and a support are possible, thereby greatly improving the quality and reliability of the medical material, which satisfies various needs of users to thus provide a good image.

BACKGROUND ART

As is generally known, collagen is a material constituting human tissue. Collagen is known to help tissue regeneration when the collagen is applied to damaged areas of the human body, and is widely used in the medical field. This is because collagen has many functional merits, such as biocompatibility, biodegradability, and tissue-restorative ability. In the medical field, currently, collagen is applied to almost all tissues of the human body, such as bone, tissue, and biological membranes.

Examples of similar technologies related to the manufacture of collagen threads in the current literature include a method of manufacturing collagen threads using dehydration, a method of manufacturing threads using electrospinning, and a method of manufacturing threads using 3D printing. In the case of the method of manufacturing the collagen threads using dehydration, the form of the threads is maintained when using only dehydration, and they are likely to be easily decomposed in the human body. In the cases of electrospinning and 3D printing, since fixing is performed so as to ensure a two-dimensional or three-dimensional structure, these cases may not be applied to the threads. Therefore, the conventional technologies seem unlikely to be applicable to the human body as medical threads.

Meanwhile, medical devices using collagen have been applied to patients in various forms. However, most medical devices remain in the form of a two-dimensional-type matrix or a three-dimensional-type support.

Further, the conventional collagen threads have drawbacks in that the collagen threads do not have sufficient strength or are soluble in water.

In order to solve the above problems, developments have been made according to the following prior art documents, but there remains still a great drawback in that the problems of the prior art are not capable of being solved through a single operation.

DOCUMENTS OF RELATED ART (Patent Document 1) Korean Laid-Open Patent Application No. 2001-0090876 (2001 Oct. 19) is published.
(Patent Document 2) Korean Laid-Open Patent Application No. 2013-0066581 (2013 Jun. 20) is published.
(Patent Document 3) Korean Laid-Open Patent Application No. 2016-0032569 (2016 Mar. 24) is published.
(Patent Document 4) Korean Patent No. 1473617 (2014 Dec. 10) is registered.
(Non-Patent Document 1) Alvin T. Yeh, Bernard Choi, J. Stuart Nelson, And Bruce J. Tromberg Reversible Dissociation of Collagen in Tissue. vol. 121, No. 6 Dec. 2003, The Society for Investigative Dermatology. 121:1332-1335

DISCLOSURE

Technical Problem

Accordingly, the present invention has been made keeping in mind the above problems occurring in the prior art, and the object of the present invention is to provide a medical material manufactured using collagen and a method of manufacturing the same. A first object is to provide collagen and a cross-linking solution including a hyperosmotic agent and a cross-linking agent. A second object of the present invention according to the above-described technical constitution is to provide a cross-linked collagen thread obtained by cross-linking the spun thread after the collagen is spun and processed into the form of a thread. The cross-linked collagen thread has increased strength compared to before cross-linking, and the shape thereof is retained in an aqueous solution. Accordingly, various applications thereof as a medical thread and a support are possible. A third object is to use the material of the present invention in the form of a thread or to use the material in the form of a fabric after weaving. Alternatively, the material is layered using 3D printing, subjected to electrospinning, or processed into various other forms. Examples of medical fields to which collagen threads provided in the forms described above are applicable include suture threads, dental materials, tissue replacement materials, adhesion bathers, hemostatic materials, drug delivery carriers, and films. A fourth object is to process a collagen thread, which has a one-dimensional structure and which is a form not mainly used in a conventional technology, according to the present invention. The collagen thread is capable of being processed into a two-dimensional or three-dimensional structure, and is also variously modified according to the needs of the consumer. A fifth object is to greatly improve the quality and the reliability of the resultant medical material, which satisfies various needs of users to thus provide a good image.

Technical Solution

In order to accomplish the above objects, the present invention includes preparing collagen using distilled water as a solvent in order to manufacture a medical material using the collagen.

Thereafter, the collagen is immediately exposed to a cross-linking solution, which is a mixture including therein a hyperosmotic agent and a cross-linking agent mixed with each other.

Subsequently, the collagen is dried, whereby a method of manufacturing the medical material using the collagen is provided.

The present invention also provides a method of manufacturing a medical material using collagen. The method includes:

(1) preparing the collagen using distilled water as a solvent, (2) filling a syringe with the prepared collagen and then spinning the collagen through a syringe needle, (3) immediately immersing the spun collagen in a cross-linking solution, which is a mixture including therein a hyperosmotic agent and a cross-linking agent mixed with each other, (4) removing and then washing the collagen after cross-linking is completed, and (5) removing and then drying the collagen after the washing is completed.

Further, the present invention provides a medical material manufactured using collagen according to the manufacturing method including steps (1) to (5).

Advantageous Effects

As described above, the present invention provides collagen and a cross-linking solution including a hyperosmotic agent and a cross-linking agent.

According to the above-described technical constitution, the present invention provides a cross-linked collagen thread obtained by cross-linking the spun thread after the collagen is spun and processed into the form of a thread. The cross-linked collagen thread has increased strength compared to before cross-linking, and the shape thereof is retained in an aqueous solution. Accordingly, various applications thereof as a medical thread and a support are possible.

In particular, in the present invention, the material of the present invention is used in the form of a thread, or the material is used in the form of a fabric after weaving. Alternatively, the material is layered using 3D printing, subjected to electrospinning, or processed in various other forms. Examples of medical fields to which collagen threads in the forms described above are applicable include suture threads, dental materials, tissue replacement materials, adhesion bathers, hemostatic materials, drug delivery carriers, and films.

In addition, a collagen thread, which has a one-dimensional structure and which is a form not mainly used in a conventional technology, is processed according to the present invention. The collagen thread is capable of being processed into a two-dimensional or three-dimensional structure, and is also capable of being variously modified according to the needs of the consumer.

The present invention having the above-described effects is a very useful invention that greatly improves the quality and the reliability of the medical material, which satisfies various needs of users to thus provide a good image.

Hereinafter, preferred embodiments of the present invention for achieving the above effects will be described in detail with reference to the accompanying drawings.

DESCRIPTION OF REFERENCE NUMERALS IN THE DRAWINGS

S 100: Step of preparing collagen
S 200: Spinning step
S 300: Immersion step
S 400: Washing step
S 500: Drying step

BEST MODE

A medical material manufactured using the collagen applied to the present invention and a method of manufacturing the same are constituted as shown in FIGS. 2 to 11.

In the following description of the present invention, if it is determined that a detailed description of a related known function or configuration may unnecessarily obscure the subject matter of the present invention, the detailed description thereof will be omitted.

In addition, the following terms are terms set in consideration of functions in the present invention, and may vary depending on the intention or custom of the producer. Accordingly, the definitions thereof should be made based on the contents throughout the present specification.

Further, since the size and thickness of each component shown in the drawings are arbitrarily shown for convenience of description, the present invention is not necessarily limited to what is shown in the drawings.

First, in the present invention, processing into a variety of forms must be performed in order to apply collagen to the human body. The present invention is technology for manufacturing a collagen thread, and the collagen thread is capable of being variously processed and applied due to the nature of the thread form. For example, the collagen may be used in the form of a thread, or may be used in the form of a fabric after being woven. Alternatively, the collagen is layered using 3D printing, subjected to electrospinning, or processed in various other forms. Examples of medical fields to which collagen threads in the forms described above are applicable include suture threads, dental materials, tissue replacement materials, adhesion bathers, hemostatic materials, drug delivery carriers, and films.

In general, in order to apply the collagen to the human body in a solid state, it is necessary to formulate the collagen into a specific form. Collagen is inherently soluble in water. In order to prevent this, a cross-linking step is required during the collagen formulation step. Cross-linking serves to induce physical and chemical bonds between collagen molecules, thus connecting the collagen molecules to each other.

Collagen that has undergone cross-linking is not easily dissolved in water and tends to increase in strength. Collagen thread, in particular, has a thin one-dimensional structure and thus the strength thereof is low. Therefore, special cross-linking measures are needed to increase the strength thereof.

Meanwhile, collagen is opaque in an aqueous solution. This is because many collagen molecules clump together in a fibrous form, causing 'collagen fiberizing'. 'Collagen fibers', generated as a result of 'collagen fiberizing', have a very dense and large structure.

When a hyperosmotic agent is added to the 'collagen fibers' that become opaque due to the 'collagen fiberizing', the 'collagen fibers' become transparent. The reason for this is that the hyperosmotic agent dissociates the 'collagen fibers' to thus maintain the form of 'collagen molecules' instead of the form of 'collagen fibers'.

In terms of cross-linking of the collagen, since the 'collagen fibers' have a very dense structure, a cross-linking agent does not penetrate the 'collagen fibers', resulting in limited cross-linking between the 'collagen fibers'. However, when the hyperosmotic agent is added, the 'collagen fibers' are dissociated, causing cross-linking between the 'collagen molecules' instead of cross-linking between the 'collagen fibers'. Accordingly, a more densely cross-linked structure is formed.

Moreover, in the present invention, the cross-linking must be performed in order to increase the strength of the collagen threads. However, the collagen molecules for performing collagen fiberizing have a very dense structure, so that the cross-linking agent does not penetrate the fibers. In order to solve this problem, the hyperosmotic agent is used to perform both dissociation of collagen fiberizing and cross-linking, thus forming a dense cross-linked structure between the collagen molecules.

The collagen that is not cross-linked is easily dissolved in water and is not strong. However, in the case of using the hyperosmotic agent and the cross-linking agent according to the above-described method, the collagen thread has a very dense cross-linked structure, so that the collagen thread is not dissolved in water and exhibits very high strength.

Figure 4:
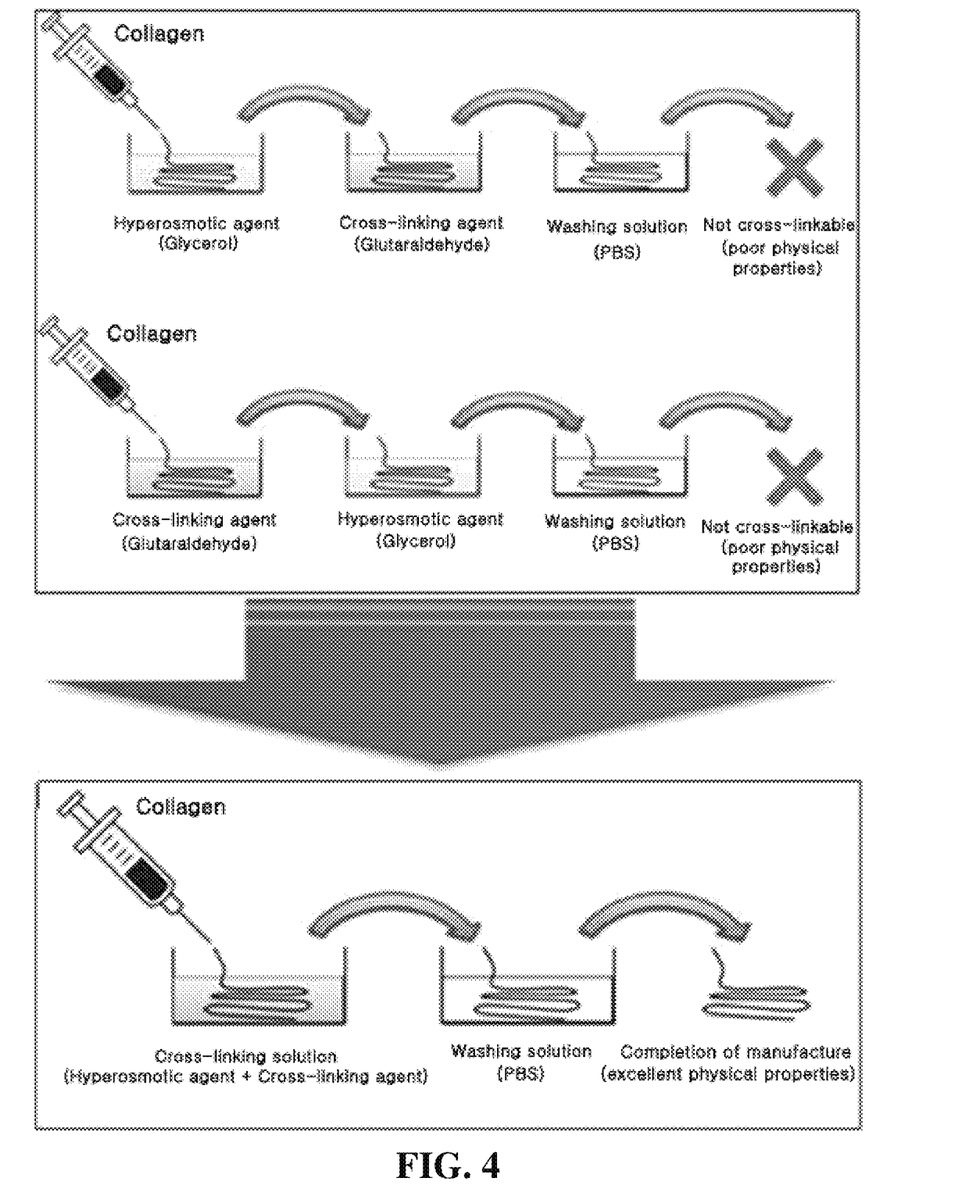
FIG. 4 is a mimetic view showing the manufacture of a collagen thread using a hyperosmotic agent and a cross-linking agent according to the present invention.

When the hyperosmotic agent was not actually used but only the cross-linking agent was used, as shown in the top picture of FIG. 4, since the collagen thread was not dissolved in water but the strength thereof was very weak, the collagen thread was inappropriate for use as a thread. Further, when the cross-linking agent was not used but only the hyperosmotic agent was used, collagen fiberizing was suppressed, but the cross-linking effect was not exhibited. However, when both the hyperosmotic agent and the cross-linking agent were used, as shown in the bottom picture of FIG. 4, it was possible to obtain a collagen thread that was not dissolved in water and had a very high strength.

Hereinafter, the manufacturing method of the present invention will be described below.

(First Constitution of the Manufacturing Method of the Present Invention)

In order to manufacture a medical material using collagen, the collagen is prepared using distilled water as a solvent.

Thereafter, the collagen is immediately exposed to a cross-linking solution, which is a mixture including therein a hyperosmotic agent and a cross-linking agent mixed with each other.

Subsequently, the collagen is dried, whereby a method of manufacturing the medical material using the collagen is provided.

(Second Constitution of the Manufacturing Method of the Present Invention)

In the present invention, in order to manufacture a medical material using collagen, (1) the collagen is prepared using distilled water as a solvent.

It is preferable that the collagen in the step (1) be included at a concentration of 1 to 15(%, w/v).

That is, when the concentration of the collagen is less than 1%, the strength required for threads or films is not ensured. When the concentration of the collagen is 15% or more, the collagen is not capable of being spun through a syringe due to the increased density thereof. Accordingly, it is preferable that the concentration of the collagen be 1 to 15 (%, w/v).

(2) A syringe is filled with the prepared collagen, and the collagen is then spun using a syringe needle.

Preferably, the spinning the step (2) is performed so that the collagen is spun into a thread and so that the spun thread has a thickness of 100 nm to 10 mm.

That is, it is possible to manufacture a thread or film having any thickness, but the thickness range that can be actually used as a thread or film is preferably 100 nm to 10 mm, which is a set range level.

(3) The spun collagen is immediately immersed in a cross-linking solution, which is a mixture including therein the hyperosmotic agent and the cross-linking agent mixed with each other.

In the case of the cross-linking solution of step (3), the ratio of the hyperosmotic agent and the cross-linking agent for manufacturing the cross-linking solution is set so that the cross-linking agent is included in an amount of 0.1 to 10% (v/v) based on the hyperosmotic agent as a solvent, and the concentration of the cross-linking solution is a concentration of glutaraldehyde including glycerol as a solvent.

In the present invention, the lower the concentration of the cross-linking solution (0.1% or less), the longer the cross-linking time, and the higher the concentration of the cross-linking solution (10% or more), the shorter the cross-linking time. Accordingly, when the concentration of the cross-linking solution is 0.1 to 10%, an optimum cross-linking time that is capable of being used industrially may be obtained. Therefore, the range of the cross-linking solution is set as described above.

In addition, the hyperosmotic agent applied to the present invention includes any one selected from among glycerol, isosorbide, mannitol, and urea.

Further, it is preferable that the cross-linking agent applied to the present invention include any one selected from among glutaraldehyde, carbodiimide, and epoxy mixtures (epoxy compounds).

In particular, it is preferable that a cross-linking time of the step (3) range from 1 minute to 48 hours.

That is, the cross-linking time varies depending on the concentration of the cross-linking solution. However, typically, when the cross-linking time is less than 1 minute, the strength is reduced. When the cross-linking time is more than 48 hours, the collagen is excessively hardened. Therefore, the range of the cross-linking time that is capable of being used industrially is preferably set to 1 minute to 48 hours.

(4) The collagen is removed and then washed after cross-linking is completed.

In the present invention, it is preferable that the washing of the step (4) include exposure to any one selected from among PBS (phosphate-buffered saline), methanol, ethanol, distilled water, acetone, distilled water, and a physiological saline solution.

(5) The collagen is removed and then dried after the washing is completed, thereby manufacturing a medical material using the collagen.

In the present invention, it is preferable that the drying of the step (5) be performed using any one selected from among freeze-drying, dry-heat drying, and natural drying.

Finally, in the present invention, the collagen may be used as any one selected from among medical threads, medical films, suture threads, dental materials, supports, tissue replacement materials, tissue-restorative materials, adhesion bathers, hemostatic materials, drug delivery carriers, and stiffeners.

Meanwhile, the present invention may be variously modified, and may take various forms in applying the above constitutions.

In addition, it is to be understood that the present invention is not limited to the specific forms referred to in the above description, but rather includes all modifications, equivalents, and substitutions within the spirit and scope of the present invention as defined by the appended claims.

The functional effects of the medical material manufactured using the collagen of the present invention constituted as described above and the method of manufacturing the same will be described below.

First, in the present invention, when the collagen is spun and processed into the form of a thread and the spun thread is then cross-linked, the cross-linked collagen thread has increased strength compared to before cross-linking, and the shape thereof is retained in an aqueous solution. Accordingly, various applications thereof as a medical thread and a support are possible.

Figure 1A:
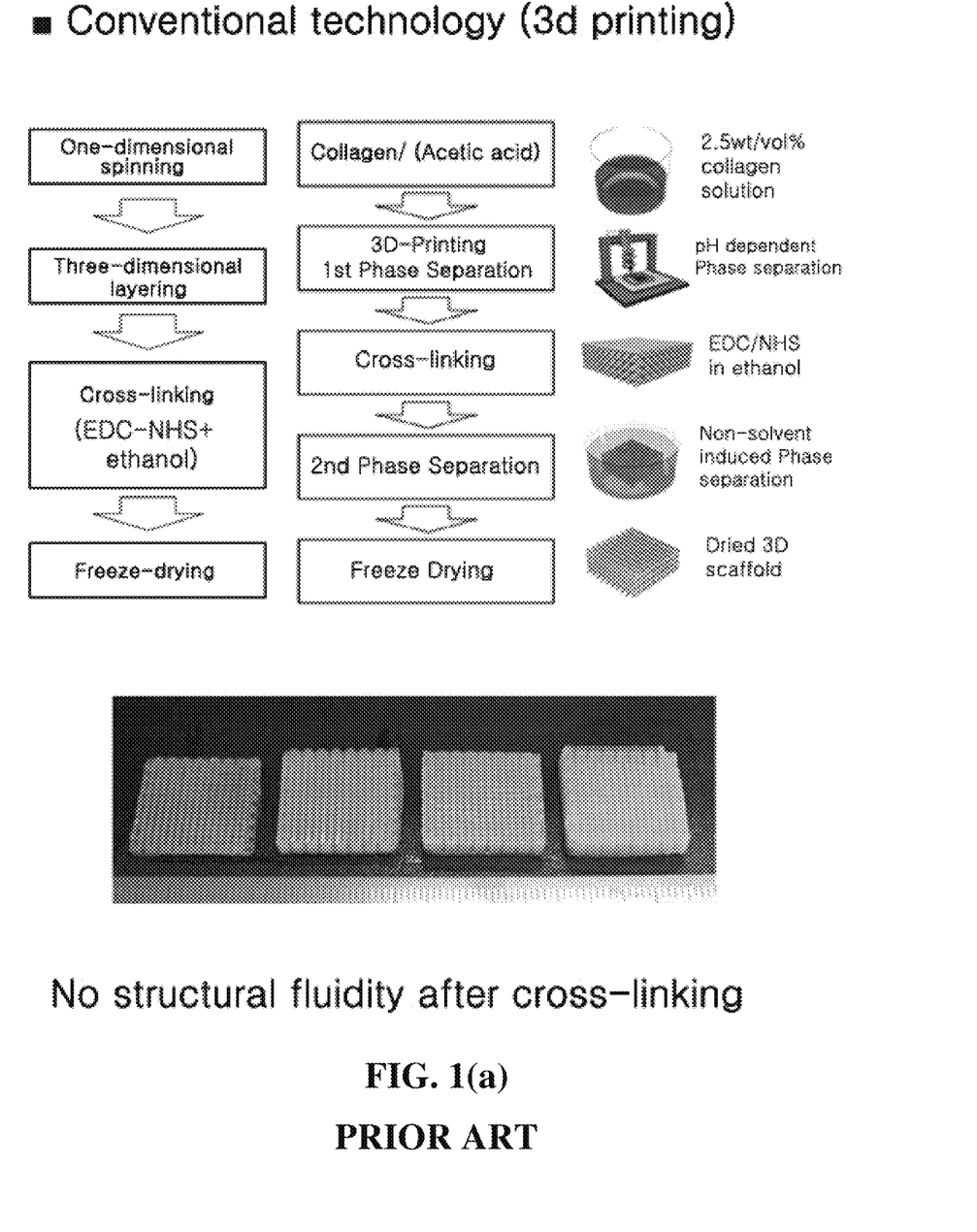
FIG. 1(a) is a view showing a manufacturing process using a conventional 3D printing technology.
Figure 1B:
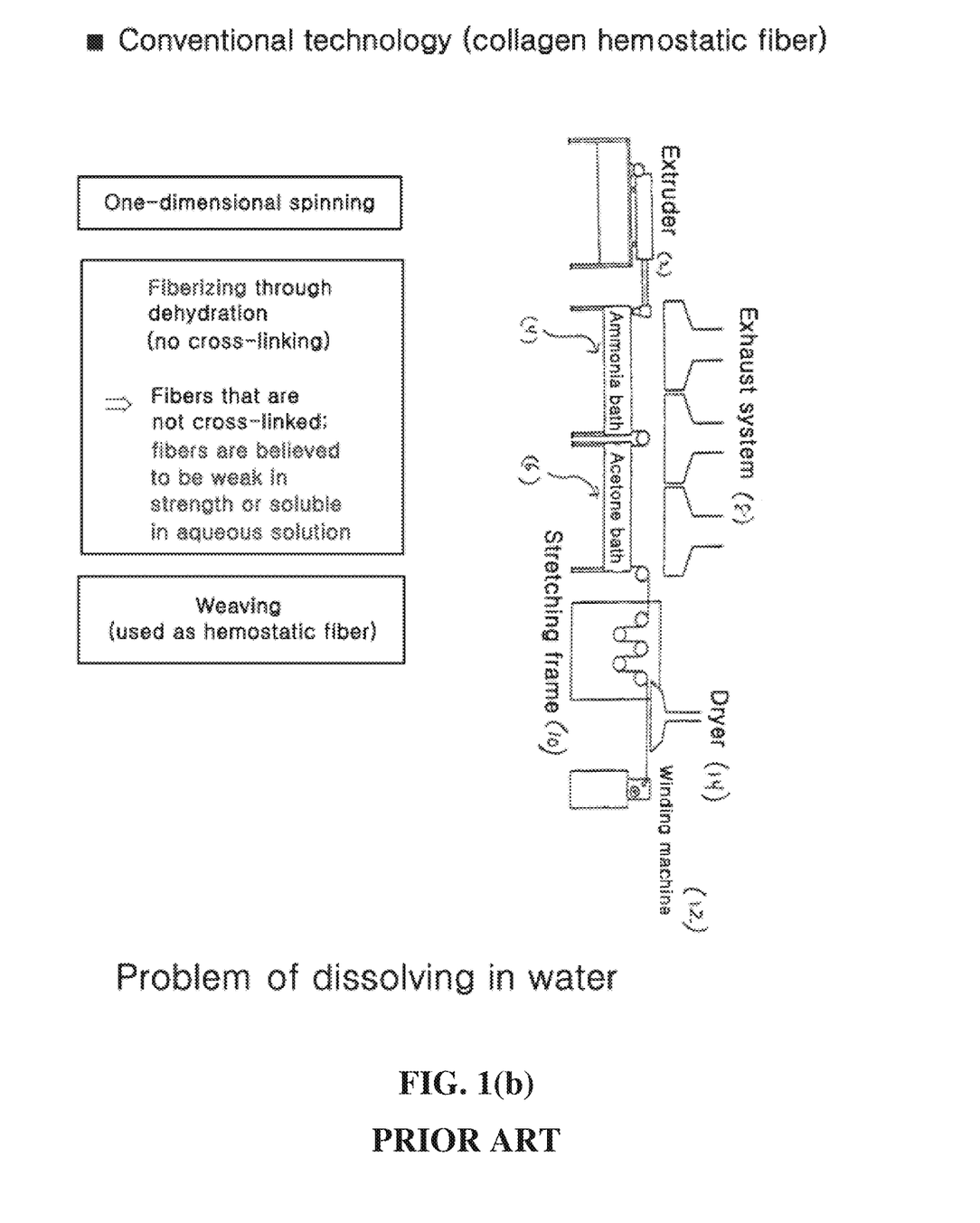
FIG. 1(b) is a view showing a process of manufacturing a conventional collagen hemostatic fiber.
Figure 2:
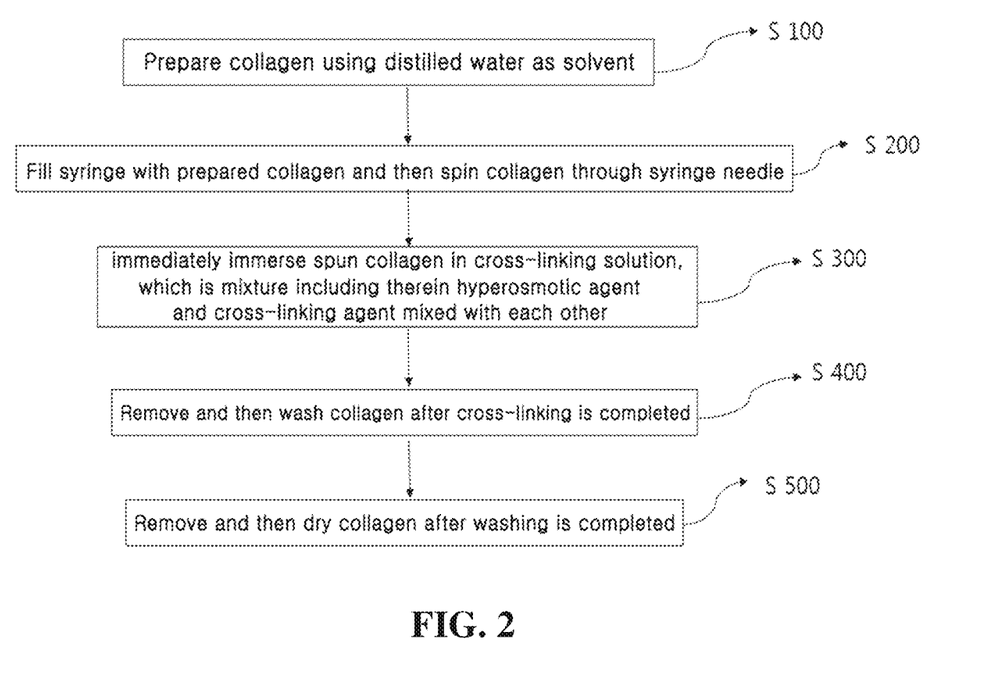
FIG. 2 is a flowchart showing a method of manufacturing a medical material
using the collagen applied to the present invention.

FIG. 2 is a flowchart showing a method of manufacturing a medical material using the collagen applied to the present invention for this purpose.

Figure 3:
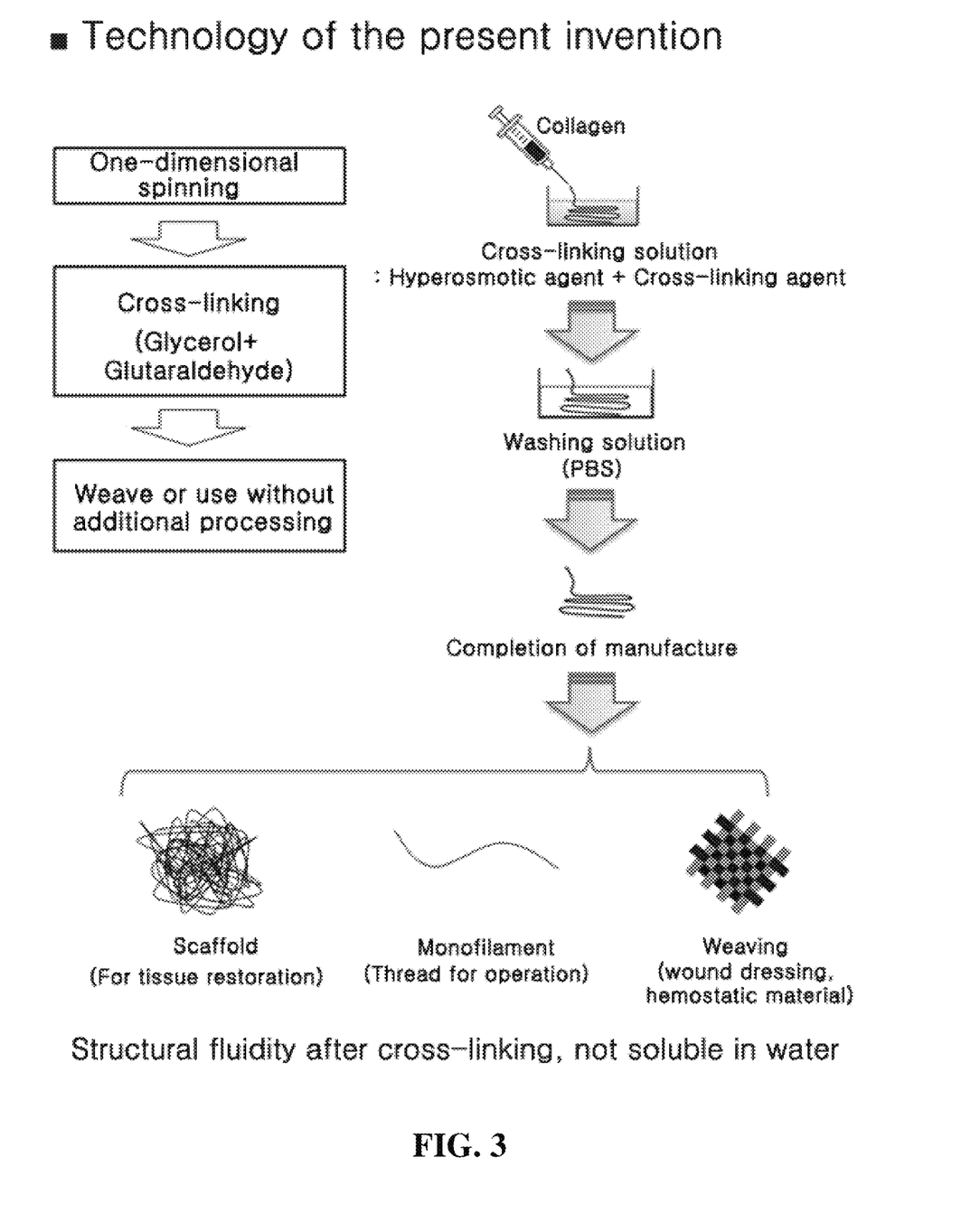
FIG. 3 is a mimetic view showing the method of manufacturing the medical material
using the collagen applied to the present invention.

In addition, FIG. 3 is a mimetic view showing the method of manufacturing the medical material using the collagen applied to the present invention. After cross-linking, structural fluidity is provided, and the collagen is not soluble in water.

Further, FIG. 4 is a mimetic view showing the manufacture of a collagen thread using the hyperosmotic agent and the cross-linking agent according to the present invention. Conventionally, it is impossible to perform cross-linking due to the poor physical properties thereof, but excellent physical properties are ensured in the present invention.

Figure 5:
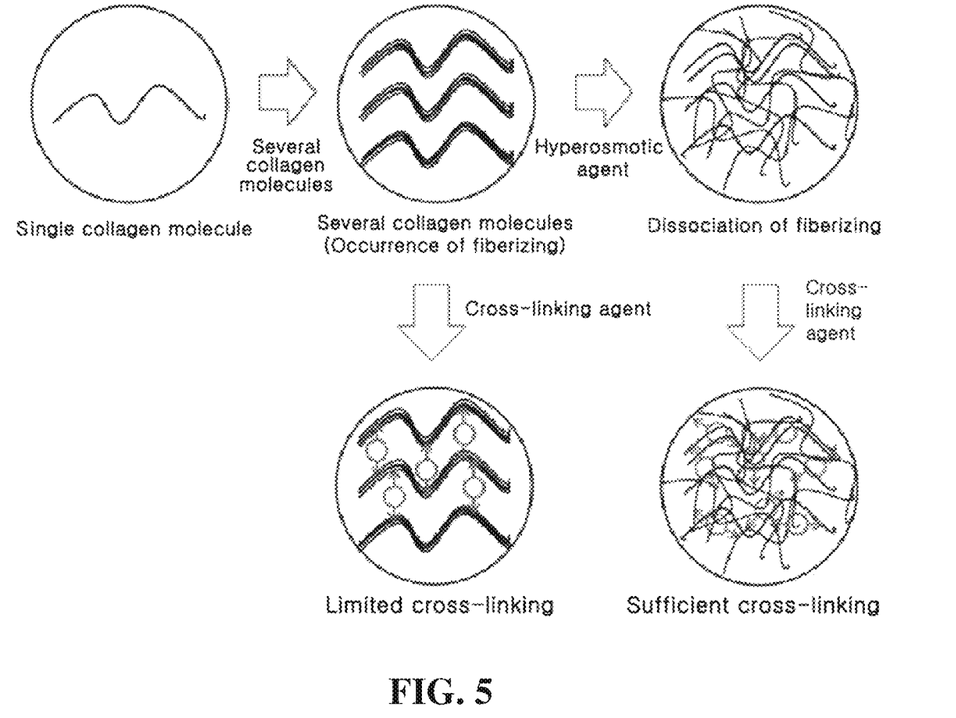
FIG. 5 is a mimetic view showing the principle of action of a cross-linking solution (a mixture solution of a hyperosmotic agent and a cross-linking agent)
according to the present invention.

In addition, FIG. 5 is a mimetic view showing the principle of action of the cross-linking solution (the mixture solution of the hyperosmotic agent and the cross-linking agent) according to the present invention, and shows limited cross-linking and sufficient cross-linking.

Figure 6:
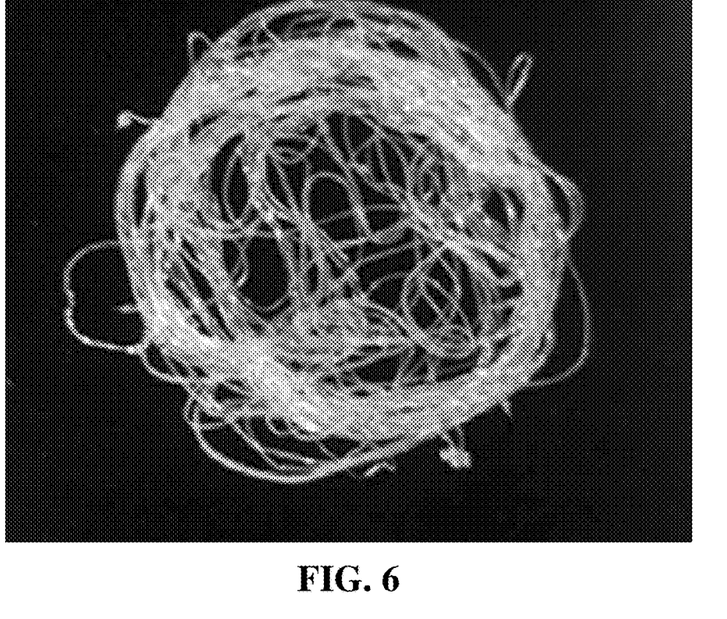
FIG. 6 shows a collagen thread manufactured according to the present invention.

Moreover, FIG. 6 is an enlarged picture of the collagen thread manufactured according to the present invention.

Figure 7:
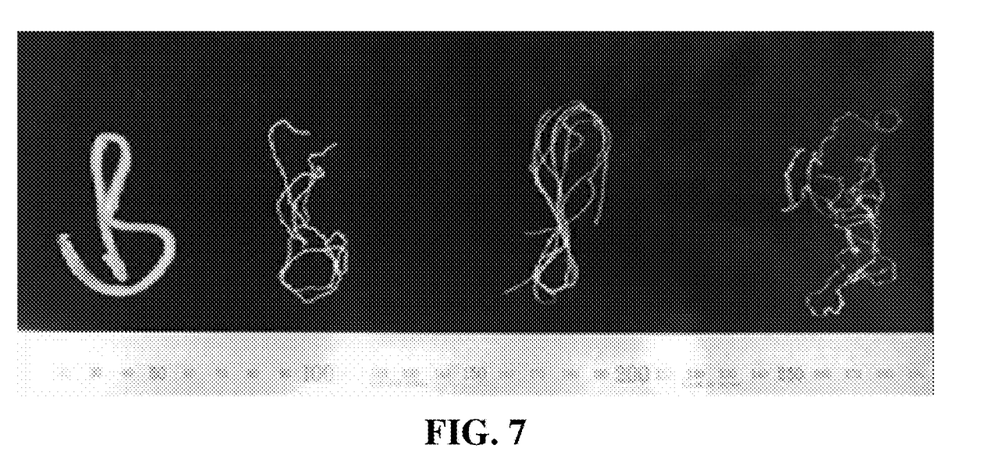
FIG. 7 shows a collagen thread spun so as to have various thicknesses according to the present invention.

In addition, FIG. 7 is an enlarged picture of the collagen thread spun so as to have various thicknesses according to the present invention.

Figure 8:
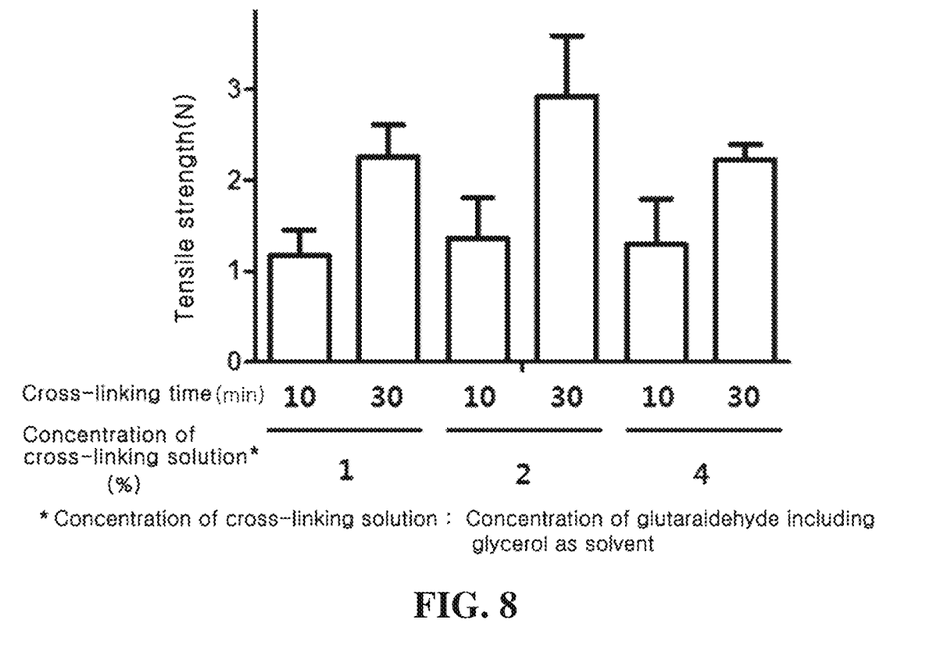
FIG. 8 is a graph showing the tensile strength of the collagen thread manufactured under various conditions.

In particular, FIG. 8 is a graph showing the tensile strength of the collagen thread manufactured under various conditions. A 9(%, w/v) collagen [g/ml*100(%, w/v), a solution containing 9 g of the collagen per 100 ml of the solution] was used. The collagen thread was manufactured for each of the conditions of the cross-linking time (10 minutes and 30 minutes) and the cross-linking solution concentration (1% (v/v), 2% (v/v), 4% (v/v) [glycerol and glutaraldehyde were mixed at volume ratios of 99:1, 98:2, and 96:4]).

The concentration of the cross-linking solution means the concentration of glutaraldehyde including glycerol as a solvent.

Figure 9:
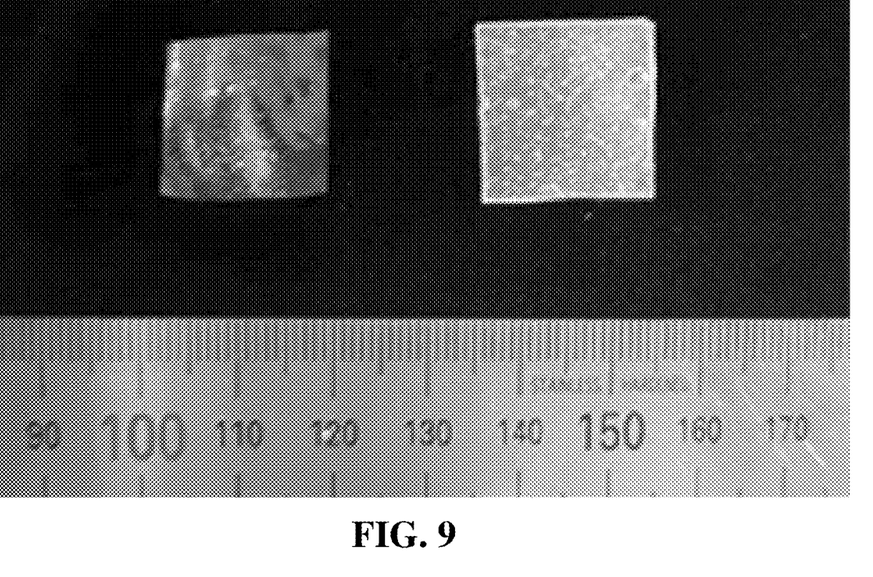
FIG. 9 shows a collagen film manufactured according to the present invention.
Figure 10:
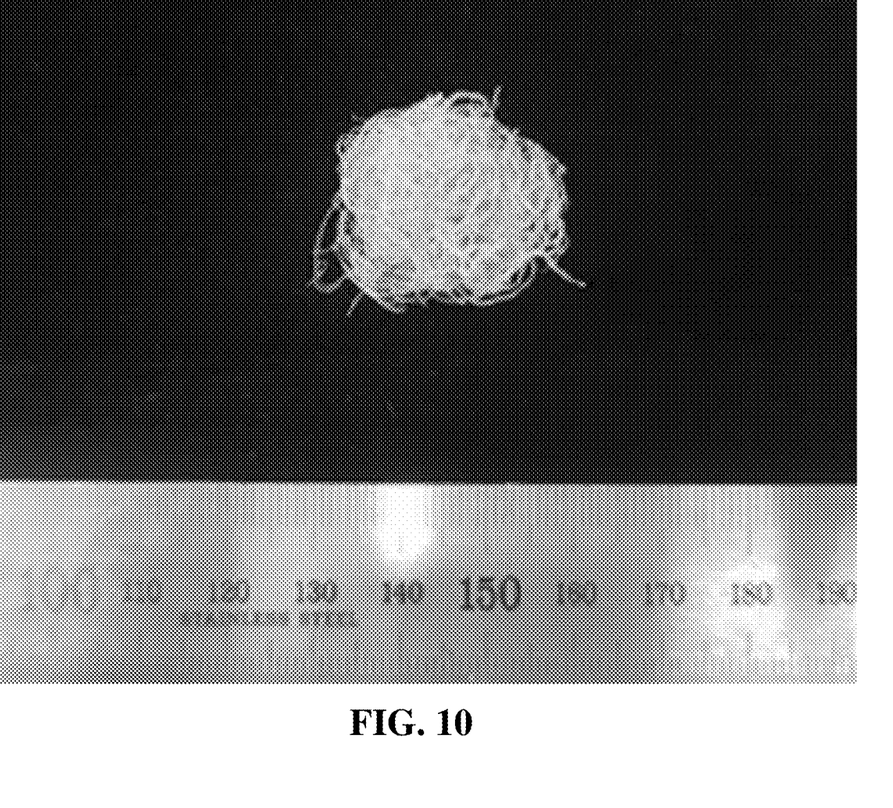
FIG. 10 shows a support manufactured according to the present invention.
Figure 11:
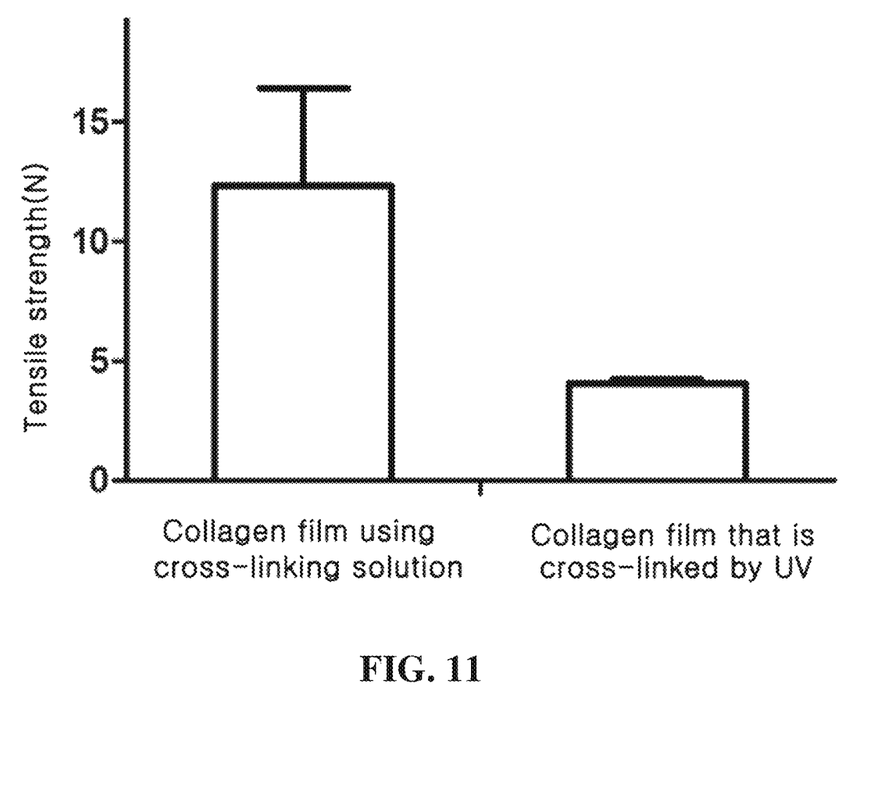
FIG. 11 is a graph showing the tensile strength of the collagen film manufactured according to the present invention.

Finally, FIG. 9 shows the collagen film manufactured according to the present invention, FIG. 10 shows the support manufactured according to the present invention, and FIG. 11 is a graph showing the tensile strength of the collagen film manufactured according to the present invention.

MODE FOR INVENTION

Hereinafter, the Examples of the present invention will be described below.

Example

First, in the present invention, collagen having a concentration of 1 to 15(%, w/v), in which distilled water is used as a solvent [g/ml*100(%, w/v), a solution containing 1 to 15 g of collagen per 100 ml of the solution], is prepared.

More preferably, collagen having a concentration of 2 to 10(%, w/v) [g/ml*100(%, w/v), a solution containing 2 to 10 g of collagen per 100 ml of the solution] is prepared.

Thereafter, in the present invention, a syringe is filled with the prepared collagen, and the collagen is then spun through a syringe needle or thinly spread on a Petri dish.

Subsequently, in the present invention, a collagen thread or film is immediately immersed in a cross-linking solution. The cross-linking solution is a solution in which a hyperosmotic agent as a solvent and a cross-linking agent at a concentration of 0.1 to 10% (v/v) are mixed [a solution in which glycerol and glutaraldehyde are mixed at a volume ratio of 99.9:0.1 to 90:10].

In the present Example, glycerol was used as the hyperosmotic agent and glutaraldehyde was used as the cross-linking agent.

More preferably, the mixing is performed at a ratio of 1 to 5% (v/v).

Thereafter, in the present invention, the collagen thread or film is immersed in the cross-linking solution for about 1 minute to 48 hours.

Subsequently, in the present invention, the collagen thread and film are removed and then washed with PBS or distilled water after cross-linking is completed.

Finally, in the present invention, the collagen thread and film are removed and then dried after the washing is completed.

In another Example of the present invention, the collagen thread and film manufactured in the above-described Example are processed into tissue-restorative biomaterials.

Examples of processing include agglomeration performed to obtain a specific shape for the purpose of use as a tissue replacement material or a support, weaving for the purpose of use as a wound dressing, a hemostatic material, or a tissue-restorative material, cutting into predetermined sizes for the purpose of use as a medical thread or a suture thread, and processing for the purpose of use as a stiffener in different types of medical devices.

In the present invention described above, the following comparison table is obtained.

TABLE 1

| Classification | Present invention | Collagen thread of similar patent | Typical medical thread | Electrospinning |
|---|---|---|---|---|
| Contents | Cross-linking after collagen is spun into threads | Dehydration after collagen is spun into threads | Threads including other polymers | Collagen and polymer are spun into a matrix form |
| Characteristics | Thread form - Tissue-restorative ability (collagen) - High strength - Not soluble in water | Thread form - Expected to be soluble in water (No cross-linking) | No tissue-restorative ability | Matrix form (not thread form) |

As a result, the cross-linking solution applied to the present invention is not provided in the conventional technology, and when the cross-linking solution of the present invention is used, the effect of imparting excellent physical properties to the collagen thread is obtained.

INDUSTRIAL APPLICABILITY

The technical idea of a medical material manufactured using collagen and a method of manufacturing the same according to the present invention is capable of repeatedly producing the same result in practice. In particular, the present invention may be carried out to promote technological development, thus contributing to industrial development. Thus, the present invention is well worth protecting.

The invention claimed is:

1. A method of manufacturing a medical material using a collagen, comprising:
   (1) preparing the collagen using distilled water as a solvent;
   (2) filling a syringe with the prepared collagen and then spinning the collagen through a syringe needle;
   (3) immediately immersing or exposing the spun collagen in or to a cross-linking solution, which is a mixture including therein a hyperosmotic agent and a cross-linking agent mixed with each other;
   (4) removing and then washing the collagen after cross-linking is completed; and
   (5) removing and then drying the collagen after the washing is completed,
   wherein:
   the hyperosmotic agent is glycerol and the cross-linking agent is glutaraldehyde, and a ratio of the glycerol and the glutaraldehyde for manufacturing the cross-linking solution is set so that the glutaraldehyde is included in an amount of 2% (v/v) based on the glycerol as the solvent.

2. A method of manufacturing a medical material using a collagen, comprising:
   preparing the collagen using distilled water as a solvent;
   immediately exposing the collagen to a cross-linking solution, which is a mixture including therein a hyperosmotic agent and a cross-linking agent mixed with each other; and
   drying the collagen,
   wherein:
   the hyperosmotic agent is glycerol and the cross-linking agent is glutaraldehyde, and a ratio of the glycerol and the glutaraldehyde for manufacturing the cross-linking solution is set so that the glutaraldehyde is included in an amount of 2% (v/v) based on the glycerol as the solvent.

3. The method of claim 1, wherein the collagen is included at a concentration of 1 to 15(%, w/v).

4. The method of claim 1, wherein the spinning of step (2) is performed so that the collagen is spun into a thread and the spun thread has a thickness of 100 nm to 10 mm.

5. The method of claim 1, wherein a cross-linking time is 1 minute to 48 hours.

6. The method of claim 1, wherein the washing of step (4) includes exposure to any one selected from among PBS (phosphate-buffered saline), methanol, ethanol, distilled water, acetone, distilled water, and a physiological saline solution.

7. The method of claim 1, wherein the drying is performed using any one selected from among freeze-drying, dry-heat drying, and natural drying.

8. The method of claim 1, wherein the collagen is used as any one selected from among medical threads, medical films, suture threads, dental materials, supports, tissue replacement materials, tissue-restorative materials, adhesion barriers, hemostatic materials, drug delivery carriers, and stiffeners.

9. A medical material manufactured using a collagen according to the manufacturing method of claim 1.

10. The method of claim 2, wherein the collagen is included at a concentration of 1 to 15(%, w/v).

11. The method of claim 2, wherein a cross-linking time is 1 minute to 48 hours.

12. The method of claim 2, wherein the drying is performed using any one selected from among freeze-drying, dry-heat drying, and natural drying.

13. The method of claim 2, wherein the collagen is used as any one selected from among medical threads, medical films, suture threads, dental materials, supports, tissue replacement materials, tissue-restorative materials, adhesion barriers, hemostatic materials, drug delivery carriers, and stiffeners.

* * * * *